(12) United States Patent
Bar et al.

(10) Patent No.: US 9,713,499 B2
(45) Date of Patent: Jul. 25, 2017

(54) ACTIVE BED MOUNT FOR SURGICAL ROBOT

(71) Applicants: Yossef Bar, Tirat Carmel (IL); Eli Zehavi, Haifa (IL); Moshe Shoham, Hoshaya (IL); David Groberman, Even Yehuda (IL)

(72) Inventors: Yossef Bar, Tirat Carmel (IL); Eli Zehavi, Haifa (IL); Moshe Shoham, Hoshaya (IL); David Groberman, Even Yehuda (IL)

(73) Assignee: MAZOR ROBOTICS LTD., Caesarea (IL)

(*) Notice: Subject to any disclaimer, the term of this patent is extended or adjusted under 35 U.S.C. 154(b) by 402 days.

(21) Appl. No.: 14/360,186

(22) PCT Filed: Dec. 5, 2012

(86) PCT No.: PCT/IL2012/000387
§ 371 (c)(1),
(2) Date: May 22, 2014

(87) PCT Pub. No.: WO2013/084221
PCT Pub. Date: Jun. 13, 2013

(65) Prior Publication Data
US 2014/0316436 A1    Oct. 23, 2014

Related U.S. Application Data

(60) Provisional application No. 61/630,102, filed on Dec. 5, 2011.

(51) Int. Cl.
*A61B 17/17*    (2006.01)
*A61B 19/00*    (2006.01)
(Continued)

(52) U.S. Cl.
CPC ...... *A61B 19/2203* (2013.01); *A61B 17/1757* (2013.01); *A61B 34/30* (2016.02);
(Continued)

(58) Field of Classification Search
CPC ............ A61B 19/2203; A61B 17/1757; A61B 2090/064; A61B 2090/571;
(Continued)

(56) References Cited

U.S. PATENT DOCUMENTS 5,408,409 A    4/1995    Glassman et al.
6,322,567 B1    11/2001    Mittelstadt et al.
(Continued)

FOREIGN PATENT DOCUMENTS

JP     H10 264061 A      10/1998
WO    WO 2006124390 A2   11/2006
WO    WO 2010064234 A2   6/2010

OTHER PUBLICATIONS

PCT International Search Report and Written Opinion of the ISA, mailed Mar. 19, 2013 in PCT/IL2012/000387.
(Continued)

*Primary Examiner* — Paula J Stice
(74) *Attorney, Agent, or Firm* — Daniel Feigelson; Fourth Dimension IP (57) ABSTRACT

A robotic surgical system incorporating a surgical robot attached to a patient's bone by an attachment member, such that motion of the bone induces corresponding motion of the robot, maintaining the robot/bone positional relationship. The robot is supported on a mechanical mounting member attached through a controlled joint to a bed-mounted base element. The controlled joint can alternatively enable the mechanical mounting member to move freely relative to the base element, or its position can be controlled by signal inputs adapted to prevent excessive force being applied in
(Continued)

the system. Two modes of operation are available (i) free motion in which the control system is decoupled from the mounting member, which rides freely with patient bone motion, and (ii) servo-controlled motion, in which drive mechanisms control the joint motion to prevent application of excessive force on the patient bone or attachment member.

20 Claims, 4 Drawing Sheets (51) Int. Cl.
*A61B 34/32* (2016.01)
*A61B 90/50* (2016.01)
*A61B 34/30* (2016.01)
A61B 17/00 (2006.01)
A61B 90/00 (2016.01)
A61B 90/57 (2016.01)

(52) U.S. Cl.
CPC .............. *A61B 34/32* (2016.02); *A61B 90/50* (2016.02); *A61B 2017/00694* (2013.01); *A61B 2090/064* (2016.02); *A61B 2090/571* (2016.02); *Y10S 901/09* (2013.01)

(58) Field of Classification Search
CPC .......... A61B 2017/00694; A61B 34/30; A61B 34/32; Y10S 901/09
USPC ........................................................ 606/130
See application file for complete search history.

(56) References Cited

U.S. PATENT DOCUMENTS

| | | |
|---|---|---|
| 6,424,885 B1 | 7/2002 | Niemeyer |
| 6,837,892 B2 | 1/2005 | Shoham |
| 7,762,825 B2 | 7/2010 | Burbank et al. |
| 7,887,567 B2 | 2/2011 | Shoham et al. |
| 8,585,420 B2 | 11/2013 | Burbank et al. |
| 9,125,680 B2 | 9/2015 | Kostrzewski et al. |
| 2007/0032906 A1 | 2/2007 | Sutherland et al. |
| 2007/0055291 A1 | 3/2007 | Birkmeyer et al. |
| 2011/0015649 A1 | 1/2011 | Anvari et al. |
| 2011/0082462 A1 | 4/2011 | Suarez et al. |

OTHER PUBLICATIONS

European Extended Supplementary Search Report of the European Patent Office in corresponding European patent application No. 12855371.6, dated Jul. 20, 2015.

ACTIVE BED MOUNT FOR SURGICAL ROBOT

This is a 35 U.S.C. §371 application of PCT/IL2012/000387, filed Dec. 5, 2012, and claims the benefit under 35 U.S.C. §120 of said PCT application, and further claims the benefit under 35 U.S.C. §119(e) of U.S. Provisional Patent Application U.S. Ser. No. 61/630,102, filed Dec. 5, 2011. The contents of these priority applications are incorporated herein by reference.

FIELD OF THE INVENTION

The present invention relates to the field of robotic surgery, especially for spinal surgery performed by a bone attached tool guide or miniature surgical robot.

BACKGROUND OF THE INVENTION

In U.S. Pat. No. 6,837,892, for "Miniature Bone-attached Surgical Robot" to one of the inventors of the present application, for there is described a miniature surgical robot attached directly to a bone of a patient, the robot's position being registered relative to preoperative images taken of the operation site. Because of the rigid attachment of the robot to the patient's bone structure, the position of the robot is fixed relative to the bone or bones to be operated on, such that motion of the patient during the operation, whether from the breathing of the patient, or whether from actual movement of the patient's body position, does not affect the position of the operating tool held by the robot relative to the bone or bones to be operated on.

In U.S. Pat. No. 7,887,567 for "Apparatus for Spinal Fixation of Vertebrae", having a common inventor with the present application, there is described an apparatus for use of surgical robot in performing orthopedic operations on the spine, using a framed device in the form of a bridge for fixing a number of vertebrae together into positions which are uniquely defined relative to the bridge, but which can move relative to the external environment. The fixation generated by such a bridge is especially useful in Computer Assisted Surgery procedures, such as by using a pre-programmed robot mounted on the bridge itself to perform the surgery. Alternative embodiments of the bridge may be used either for performing surgery in one procedure on a number of vertebrae of the spine, or as a reference frame for performing surgery at different locations along the spine, while providing an alignment reference along major lengths of or along all of the spine. These systems are also characterized in that they enable the performance of minimally invasive procedures, with the robot supported by clamps having small cross sections, attached to the bone or bones on which the surgical procedure is being performed.

However, in either of the systems described in the above referenced prior art, if the robot is attached rigidly to the patient's bone, either directly to the bone, or on a structure such as a bridge attached rigidly to the bone, and significant force is exerted by the surgeon onto a surgical tool, such as a surgical drill, there is a danger that the force of the tool on the bone, or the components of side forces on the drill guide transferred to the bone-mounting element, may be sufficient in some cases, to detach the attachment clamp from the bone, such that the robot position is no longer defined relative to the bone. Even if complete detachment does not occur, the exerted force may be sufficient to overcome the clamping friction of the clamp with the bone, and thus to shift the position of the clamp on the bone, with the same end result of loss of positional relationship between the robot and the bone. Furthermore, even if no movement of the clamp from the bone occurs, such excessive force may result in bending of the mechanical attachment member connecting the bone to the robot or the robot support, such that this too would cause the loss of the defined spatial relationship between the robot coordinate system and the bone.

There therefore exists the need for a robotic surgical system that can overcome at least some of the above mentioned disadvantages of prior art systems, such as an ability to withstand high forces exerted on the robot while still maintaining minimally invasive bone clamping techniques.

The disclosures of each of the publications mentioned in this section and in other sections of the specification, are hereby incorporated by reference, each in its entirety.

SUMMARY

The present disclosure describes a new exemplary system for operations performed using a surgical tool guide attached to a robotically controlled arm which can compensate for bodily motion of the region on which the surgical tool is operating. The system enables the tool guide to be coupled to the body structure being operated on, which is commonly a bone structure, such that motion of this bodily structure induces corresponding motion of the tool guide itself, such that the positional relationship of the tool guide to the body structure being operated on is maintained. Since a common use of the system is for orthopedic operations, it will be generally described in this disclosure for such use, whereby the positional relationship of the tool guide has to be maintained relative to the bone being operated on.

The system differs from prior art systems, such as those described in the above referenced patent documents, in that the tool guide is jointly supported by both (i) a rigid mechanical attachment element, attaching the tool guide or a structure on which the tool guide is mounted, to the bone or bones being operated on and thus providing mechanical spatial correlation to the bone, and, in addition, (ii) a mechanical mounting member attached through a dual-function controlled coupling joint to a static base element. The double-functionality of this coupling joint is that in one configuration, it can be an adaptable motion joint, enabling the mechanical mounting member to move freely relative to the base element, and in its alternate function, it can become a rigid joint whose motion is controlled by means of control signal inputs. The static base element may be advantageously mounted either to the bed on which the subject is lying, or to the floor or ceiling of the operating room in the vicinity of the bed, though other attachment points can also be used. If not mounted directly to the bed, then the alternative mounting point should be in a fixed position relative to the position of the bed. For convenience, the term bed-mounted will be used herewithin to denote the mounting position of the base element, though it is to be understood that this term is intended to cover any static mounting configuration relative to the bed on which the patient is lying.

The use of this second mounting arrangement at the static base element provides the tool guide with additional mechanical support which can be used to assist in preventing pull-out, buckling, or shift of the mechanical attachment element attached to the bone, if excessive force is applied to the clamped bone from a tool held or guided by the tool guide. The pull-out safety protection provided by the system also enables an even less invasive approach to be used in such orthopedic operations, such as only a single K-wire rather than a bone clamp or several K-wires or pins. The described system is particularly useful for orthopedic operations in which considerable force may be required by the surgeon when drilling or reaming holes into the bone or bones which are being operated on. In such cases, the tool guide supported on the robotically controlled arm may be subject to considerable lateral forces, which, because of the connection of the mechanical mounting member to the subject's bone through the attachment element, may cause the attachment to the bone to be loosened or completely separated, or may cause the attachment member to deform or bend. In any of these cases, the positional relationship between the tool guide and the subject's bone will be lost, such that the accuracy of the operation will be lost.

In order to enable the tool guide to continue to move freely with movement of the patient, as previously mentioned, the mounting member is attached to the base element through a dual purpose, controlled coupling joint which both enables the mounting member to freely follow the patient bone motion, and in addition, can lock into a controlled mode in order to resist excessive applied force. This joint can be based on one or more of swiveling, spherical or translational joints, or a combination thereof, such that although the base element itself is static, the mounting member can move freely relative to the base element with motion of the bone of the patient, such as rising and falling with the breathing motion of the patient. So long as excessive forces are not applied by the surgical tool onto the bone of the patient, this is the status of the system, with the tool guide and its mounting member moving freely in unison with movement of the patient.

In order to ensure that excessive forces are not applied to the K-wire or any other clamping device used to correlate the position of the tool guide to the bone structure of the subject, the system also incorporates an active feedback mechanism. One or more controlled motor drives are incorporated into the base element or the mounting member, to control the position or force/moment of the controlled joint or joints attaching the mounting member to the static base element. So long as the force being applied by the surgical tool is less than the predetermined threshold, the control motor drives are declutched or disconnected or free-running by use of a back drivable servo system, and allow the mounting member with the tool guide to move freely and uncontrolled with motion of the patient.

Once an excessive force is detected, these motor drives apply a reactive force to the mounting member to counteract force above the predetermined threshold level exerted by a surgical tool held in the tool guide, onto the bone being operated on. The control input to this motor drive may be obtained by a force sensor incorporated in the clamping path used to attach the tool guide to the bone structure of the subject, most conveniently in the rigid mechanical attachment element itself. When this sensor indicates that the force applied to the tool exceeds a predetermined level such that it is likely to cause the mechanical attachment element to become detached from the bone structure, or to be sufficiently loosened that it can move relative to the bone structure, or may cause the tool guide support or the mechanical attachment element to flex, a feedback signal is applied to the control motor drive, which acts in the opposite direction to the force applied to the tool guide, and counteracts the excessive force applied. This should prevent the mechanical attachment member from moving or becoming detached, or from it or the other mechanical parts from bending. In its simplest implementation, this control function is only activated if the force exerted on the rigid mechanical attachment element exceeds the predetermined threshold level. Up to that level, the control system is inactive, and the mounting member and hence the tool guide move freely with movement of the patient.

This combined support mechanism for the tool guide therefore has a double function. Firstly, when excessive forces are not applied by the surgeon, it ensures that the spatial position of the tool guide is maintained relative to the bone structure being operated on, such that if the bone structure moves because of the patient's breathing or motion, the tool guide moves in sympathy. At the same time, if excessive forces are applied by the surgeon, the system has an actively controlled motion applied to it, relative to the static base element, such that these excessive forces cannot be conveyed to the bone attachment element. This combined system thus ensures that the advantages of the prior art bone mounted surgical robotic technologies, namely positional correlation of the surgical tool with the bone, are maintained, in combination with a controlled level of mechanical flexibility that provides an additional safety level to the operating procedure, regardless of the force used by the surgeon in handling of the surgical tool. Also with this mechanism, minimally invasiveness is maintained and even enhanced, as the clamping device can be smaller since it need not bear the full load applied to it by the surgical tool.

The effect of the control mechanisms on the motion of the mounting member can have a number of different options as follows:
  (i) A vertical linear drive only may be used, allowing the end of the mounting member at its bed mounted end, to rise and fall vertically.
  (ii) A swivel joint only may be used, allowing the end of the mounting member at its bed mounted end, to swing angularly in a vertical plane.
  (iii) Both translation and swivel joints may be used, allowing the end of the mounting member at its bed mounted end to swing and translate vertically.
  (iv) In addition to the above options, a universal joint or a combination of two serial rotary joints may be used, allowing the end of the mounting member at its bed mounted end to move horizontally also, enabling the surgeon to move the tool guide sideways to any position where the he needs to operate, without losing the spatial correlation between the tool guide co-ordinate system and the bone.
  (v) Any other combination of controlled joints may also be proposed to provide even more flexibility of motion of the mounting member, while maintaining the connection with the bone.

In the above described implementations, the controlled joint has two separate modes of operation:
  (i) a completely free motion mode in which the drive mechanisms do not control the mounting member at all, and the mounting member rides freely with patient bone motion, and
  (ii) a servo-controlled motion mode, in which the drive mechanisms control the joint motion to prevent application of excessive force on the patient bone or elsewhere.

In an alternative implementation, the drive mechanisms are coupled and activated all the time, the positioning input to the control system being a follower sensor which determines the position of the patient's bone, and activates the drive mechanisms to move the mounting member positively such that it follows this movement of the bone, preferably without imposing noticeable restraints on the bone. This mode of operation continues so long as the predetermined load on the K-wire or other connection to the bone is not exceeded. The moment such an excess load is detected, the control system reverts from a follower mode to a positive control mode, and operates, as described previously, to oppose the motion of the mounting member in order to reduce the load on the K-wire or other element, to below the allowed level. It is to be emphasized in passing that the function of this follower mode of operation is not to input information about the position of the bone relative to the robot position, such as is provided by the prior art bone followers of the type described in U.S. Pat. No. 6,322,567 for "Bone Motion Tracking System" to B. D. Mittelstadt et al., since in the present system, the mounting of the robot in a predetermined fixed position relative to the bone, makes this function unnecessary. As the robot follows freely the motion of the bone the follower is merely used as a feedback mechanism to activate the motors in order to positively oppose excessive force applied to the robot.

The above exemplary system and its operation modes have been so far described in terms of a tool guide held on the end of the articulated arms attached to the mechanical mounting member. The tool guide can be aligned in its desired orientation by the surgeon, generally using his experience and visual capacities, possibly assisted by pre-operative or intraoperative images of the operation site, or a or navigation device. Alternatively, a miniature surgical robot can be mounted on the articulated arms or the mechanical mounting member, and the position and orientation of the tool guide adjusted using inputs to the miniature surgical robot.

Furthermore, since the most common use of this type of system is in orthopedic surgery, where the forces that may need to be applied are considerable and may thus cause mechanical detachment or flexing, such orthopedic implementations have been used in this disclosure to describe the system and its various uses. However, it is to be understood that such systems are not limited to bane attached situations, and can equally well be used for surgical procedures on soft tissue or organs, where the need may also exist to maintain positional correlation between the surgical tool and the tissue being operated on. In such cases, the forces concerned will generally be much lower and the structures consequently will be much lighter and more sensitive. Likewise, the attachment member will need to be different from the k-wire or other mechanical bone attachment elements described above, and will generally more resemble a needle based structure, equipped with a sensor to sense force or displacement as a result of force applied by the surgeon on the operated organ.

There is thus provided in accordance with an exemplary implementation of the devices described in this disclosure, a system for performing an orthopedic operation on a subject, the system comprising:
  (i) a mechanical mounting member adapted to support a surgical tool guide for use in operating on the subject,
  (ii) a support member rigidly positioned relative to the bed on which the subject is lying, the mechanical mounting member being attached to the support member by a moveable element,
  (iii) a bone attachment element adapted to attach the mechanical mounting member to a bone of the subject in the region where the orthopedic operation is to be performed, such that the mechanical mounting member and its supported tool guide can move with motion of the bone of the subject,
  (iv) a force sensor associated with the bone attachment element, the force sensor adapted to output a force signal in accordance with the force exerted on the bone attachment element, and
  (v) control circuitry receiving the force signal and adapted, when the force exceeds a predetermined threshold level, to output a drive signal to actuate motion of the moveable element such that the mechanical mounting member moves in a direction to reduce the level of the force.

In such a system, the moveable element may comprise a linear motion slide, such that the mechanical mounting element can move translationally relative to the support member. Alternatively or additionally, the moveable element may comprise an angular pivot joint, such that the mechanical mounting element can pivot relative to the support member.

Furthermore, the tool guide may be mounted either directly on the mechanical mounting member or on a robot attached to the mechanical mounting member. The robot may comprise a serial arrangement of controlled articulated arms attached to the mechanical mounting member.

In any such systems, the bone attachment element may conveniently be a K-wire.

Additional implementations may involve a system as described hereinabove, wherein the movable element may be adapted to enable the tool guide to rise and fall together with vertical motion of the bone of the subject when the controlled motion drive is not actuated. In such a case, the controlled motion drive may be set in a free-running condition when the force is less than the predetermined threshold level, such that the mechanical mounting member can move freely with motion of the bone.

In any of the above described exemplary systems, the motion of the moveable element may be actuated through a controlled motion drive.

Additionally, an alternative implementation of the systems described in this disclosure may involve a system for performing surgery on a subject, the system comprising:
  (i) a mechanical mounting member adapted to support a surgical tool guide for use in operating on the subject,
  (ii) a support member rigidly positioned relative to the bed on which the subject is lying, the mechanical mounting member being attached to the support member by a moveable element,
  (iii) a tissue attachment element adapted to attach the mechanical mounting member to a tissue of the subject in the region where the surgery is to be performed, such that the mechanical mounting member and its supported tool guide can move with motion of the tissue of the subject,
  (iv) a force sensor associated with the tissue attachment element, the force sensor adapted to output a force signal in accordance with the force exerted on the tissue attachment element, and
  (v) control circuitry receiving the force signal and adapted, when the force exceeds a predetermined threshold level, to output a drive signal to actuate motion of the moveable element such that the mechanical mounting member moves in a direction to reduce the level of the force.

Yet other implementations perform a method of performing orthopedic surgery on a subject, the method comprising:
  (i) supporting a surgical tool guide on a mechanical mounting member, for use in performing the surgery,
  (ii) attaching an end of the mechanical mounting member remote from the tool guide, to a support member rigidly positioned relative to the bed on which the subject is lying, by means of a moveable element, (iii) attaching a bone attachment element between the mechanical mounting member and a bone of the subject in the region where the orthopedic surgery is to be performed, such that mechanical mounting member and the tool guide can move together with movement of the bone of the subject, (iv) measuring the force present in the bone attachment element, and (v) if the force exceeds a predetermined threshold level, moving the moveable element such that the mechanical mounting member moves in a direction to reduce the level of the force.

In such a method, the moveable element may comprise a linear motion slide, such that the mechanical mounting element can move translationally relative to the support member, and/or an angular pivot joint, such that the mechanical mounting element can pivot relative to the support member.

Furthermore, in this method, the tool guide may be mounted directly on the mechanical mounting member, or it may be mounted on a robot attached to the mechanical mounting member. Such a robot may comprise a serial arrangement of controlled articulated arms attached to the mechanical mounting member.

In any of these methods, use may be made of a K-wire as the bone attachment element.

Additional implementations may involve a method as described hereinabove, wherein the movable element may enable the tool guide to rise and fall together with vertical motion of the bone of the subject when the controlled motion drive is not actuated. In such a case, the controlled motion drive may be set in a free-running condition when the force is less than the predetermined threshold level, such that the mechanical mounting member can move freely with motion of the bone.

In any of the above described methods, the motion of the moveable element itself may be actuated through a controlled motion drive.

Additional methods may involve performing surgery on a subject, the method comprising:

(i) supporting a surgical tool guide on a mechanical mounting member, for use in performing the surgery, (ii) attaching an end of the mechanical mounting member remote from the tool guide, to a support member rigidly positioned relative to the bed on which the subject is lying, by means of a moveable element, (iii) attaching a tissue attachment element between the mechanical mounting member and a tissue of the subject in the region where the surgery is to be performed, such that mechanical mounting member and the tool guide can move together with movement of the tissue of the subject, (iv) measuring the force present in the tissue attachment element, and (v) if the force exceeds a predetermined threshold level, moving the moveable element such that the mechanical mounting member moves in a direction to reduce the level of the force.

BRIEF DESCRIPTION OF THE DRAWINGS

The present invention will be understood and appreciated more fully from the following detailed description, taken in conjunction with the drawings in which.

DETAILED DESCRIPTION

Figure 1:
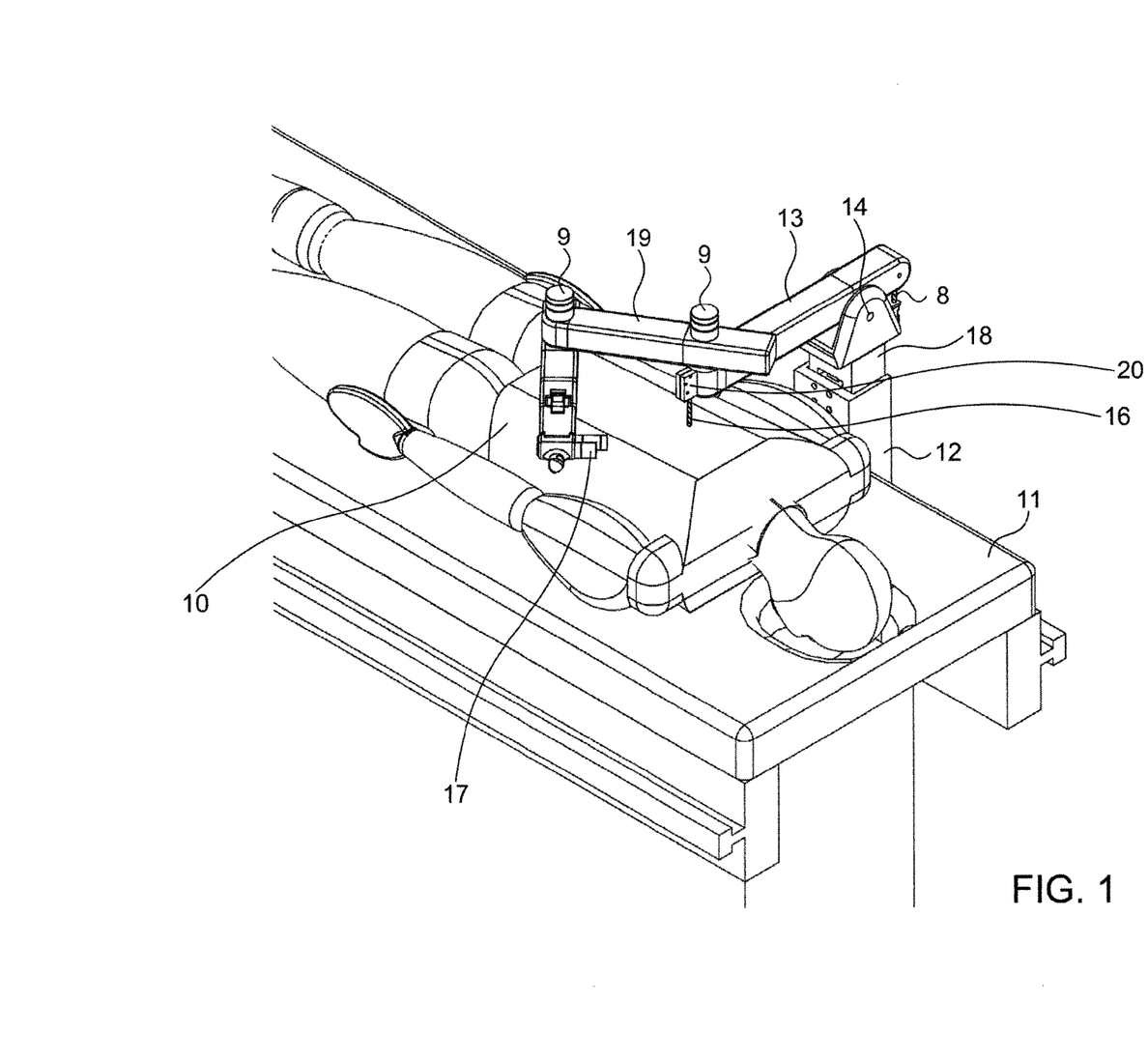
FIG. 1 shows schematically an exemplary system for performing robotically guided operations on a subject, using an active bed-mounted robot.

Reference is now made to FIG. 1, which illustrates schematically a first exemplary system for performing robotically guided operations on a subject, using an active bed-mounted system, as described in the present application. In the example of FIG. 1, and of the other drawings in this disclosure, the system is shown performing orthopedic surgery on the patient's spine, though it is to be understood that this is only one possible use of such a system, and it is not intended to limit the application in any way. The robot shown in this exemplary system comprises a linked series of articulated arms 19, coupled together by means of controlled angular motion links 9, such that the complete arm system generates the robotically controlled motion. A surgical robotic actuator 17 or a simple tool guide is shown at the extremity of the controlled articulated arms 19. The robotic arm system 19 is supported on a mechanical mounting member 13. Such an articulated arm robotic system 19 is only one exemplary method of providing controlled robotic motion to the surgeon, and it is to be understood that any other suitable robotic system may also be used in such applications. For instance, as will be shown in FIG. 2 hereinbelow, it is possible to attach a conventional miniature surgical robot, whether parallel or serial or hybrid, directly to the mounting member 13, and to control the robotic surgery through the miniature robot itself.

The patient 10 is shown lying on the operating bed 11, with the base element 12 of the mechanical mounting member shown attached to the bed 11. However, it is to be understood that this is only one possibility for attachment of the mechanical mounting member base, and that the invention is not intended to be limited by this mounting method. In the system shown, the mechanical mounting member 13 is attached to the base element 12 through a support element 18 and the mechanical mounting member itself 13, attached to this support element 18 through a joint 14, which allows the mechanical mounting member 13 to pivot relative to its support element 18. The pivoting action of the joint can be either free running, or it can be controlled by means of a motor controlled actuator 8, mounted in the pivot joint base. Although this pivot joint, when fitted, can provide an angular element of freedom for the mechanical mounting member, the support element 18 can, in addition or alternatively, be provided with a translational slide feature, such that it can slide vertically within the base 12, such the entire mechanical mounting assembly can move vertically with vertical movement of the patient 10. Thus, when no control is exerted on the mechanical mounting member, it can perform either or both of pivoting and translationary motion to follow movement of the patient. For the example of spinal surgery, one end of a rigid mechanical attachment element, shown in FIG. 1 as a K-wire 16, is shown attached to the bone structure of the patient on which the operation is to be performed, and the other end of the rigid mechanical attachment element is attached to the mechanical mounting element 13 at the end closer to the robot mounting position. The systems are described from here onwards in this disclosure, using a K-wire rigid mechanical attachment element, as shown in FIG. 1, though it is to be understood that this is only one possible method of implementing the connection of the bone to the robot system. The example in FIG. 1 shows the setup for performing an operation on the patient's spine. The effect of the K-wire rigid mechanical attachment element is to make sure that as the patient breathes, and the K-wire moves up and down with the patient's breath, the mechanical mounting member 13 supporting the robotic actuator 17 or tool guide also moves up and down with the movement of the spine of the patient, either by pivoting or by vertical translation, or by a combination of both.

In FIG. 1, no details are shown of the way in which the control circuitry and feedback system operates, and the mechanical mounting member 13 is shown freely moveable vertically within the bed-mounted base 12. In order to prevent excessive forces from being applied by the surgeon to the patient, control motors are incorporated into the mechanical path between the mechanical mounting arm 13 and the bed mounted base 12. As previously mentioned, a number of different possibilities exist as to how this may be implemented in practice. In order to simplify an understanding of the manner of operation of the system, as a first implementation, only control over the vertical linear motion of the mechanical mounting arm will be used to describe the system operation.

Figure 2:
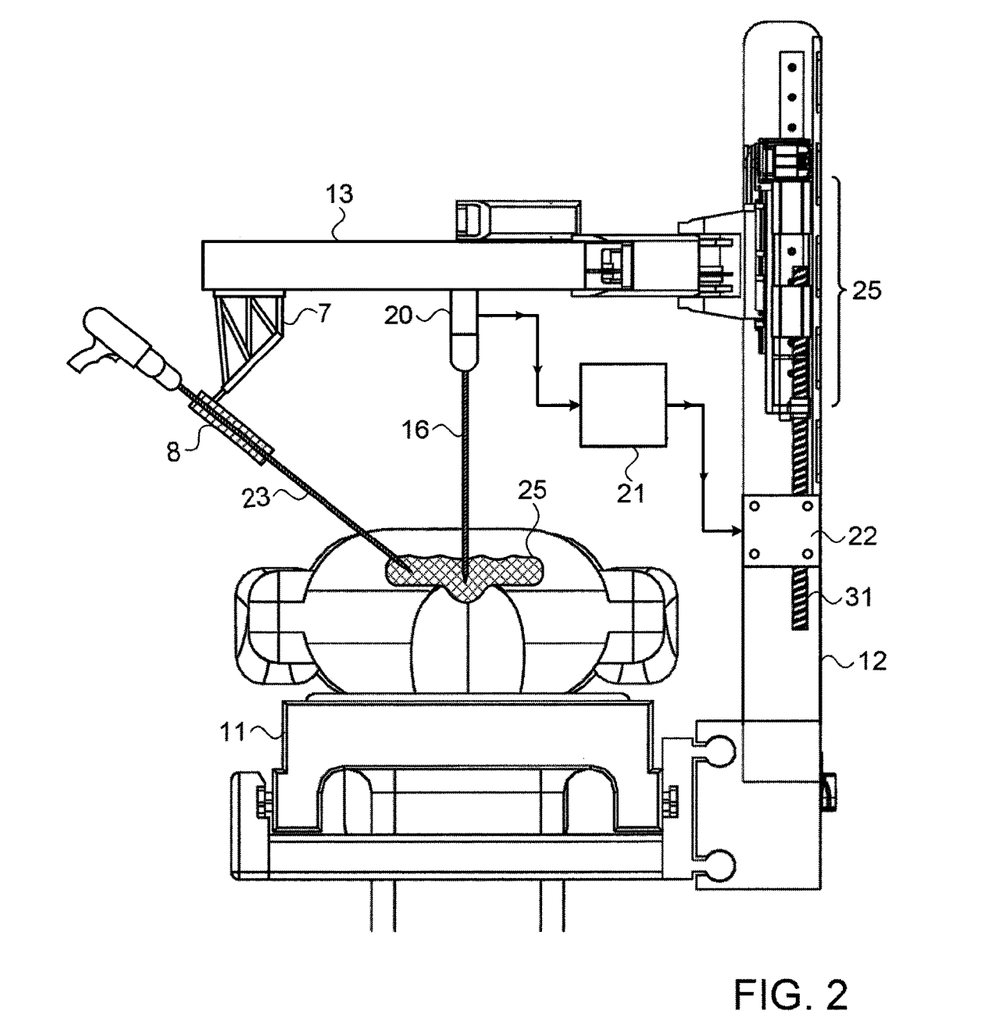
FIG. 2 illustrates schematically the control circuit elements operating in order to prevent excessive forces from being applied during the operation.

Reference is now made to FIG. 2, which illustrates how the control circuits operate in order to prevent excessive forces from being applied to the K-wire attaching the mounting member to the bone structure being operated on. FIG. 2 shows an exemplary system in which the mechanical mounting member 13 has a single controlled joint 25 allowing it to move linearly within the bed mounted base 12. The robot used, unlike that of FIG. 1, is a compact miniature surgical robot 7 supported directly on the end of the mechanical mounting member 13. A force sensor 20 is attached to the K-wire 16, preferably between the K-wire and its attachment to the mechanical mounting member 13, in order to measure the force being applied on the K-wire 16. Using as an example, the drilling of a hole in a vertebra 25 of the subject using the robot 7 to provide the correct entry path, as a surgeon applies pressure on the drill 23, whether the drill is held directly in the robot or in a drill guide aligned by the robot, tension or compression will be applied to the K wire 16, as the drill 23 may not be perfectly aligned with the drill guide axis, and side pressure is exerted on the guide. This force is measured by the force sensor 20, whose output signal is input to the system controller 21. So long as the force in the K-wire does not exceed the predetermined threshold level, the control system is not activated, allowing the mechanical mounting member to move freely along the length of the bed mounted base 12. However, if the force exceeds that predetermined threshold level, the feedback circuit of the system controller 21 outputs a correction signal to the control motor drive 22, which operates to move the mechanical mounting member 13 in such a direction as to prevent the force in the K-wire from exceeding that predetermined level, this level being selected in order to prevent the K-wire or other clamping mechanism from being pulled out or forced into the vertebra 25 of the subject by the drilling force applied by the surgeon or to prevent flexing of either the robot supports or its bone support beyond allowed accuracy margins. In FIG. 2, the servo motor 22 is shown driving a lead screw 31 which couples directly to the mechanical mounting member 13. The free linear motion of the mechanical mounting member 13 can most conveniently be accomplished by using a back drivable servo system, such as a ball screw drive, or by declutching the member itself from the lead screw, so that it can move freely up or down the bed mounted base 12. However, it is to be understood that this is only one example of the way in which the mechanical control of the vertical motion of the mechanical mounting member 13 can be achieved, and the invention is not intended to be limited to this example.

As an example to explain the operation of the feedback correction mechanism, the case is considered of the surgeon using a drill 23 aligned by a robot-positioned drill guide 8. As the surgeon exerts force on the drill, that force may not be perfectly aligned with the drill guide. Because of the downward direction of the pressure of the surgeon on the drill, the most common situation is for the drill to be pushed at an angle further away from the vertical than the positioned angle of the drill guide. The force exerted by the drill on the drill guide can then be resolved into a horizontal component and a downward vertical component on the K-wire, which may result in compression and bending forces being applied to the K-wire. When these forces reach a level above the predetermined threshold, the control system is activated, and applies a reaction force to the mounting member 13 that is transferred to the drill guide to alleviate the compressive load on the K-wire. Once this compression falls below the predetermined level, the control motion of the motor 22 ceases, and the surgeon continues his drilling without the danger that the K-wire will be pushed into the patient's vertebra 25 or flexed beyond its allowed threshold. If, on the other hand, the surgeon inadvertently applies pressure to the drill at an angle closer to the vertical than the alignment of the drill guide, then the forces on the K-wire are reversed, and there is a tendency to apply a tensile force on the K-wire, and to detach it from the vertebra, and it is this force which the control system is then required to compensate. The whole process is transparent to the surgeon who simply continues drilling in his regular manner, while the control system ensures the integrity of the mechanical connection between the bone of the patient and the robot end of the mechanical mounting member 13.

Figure 3:
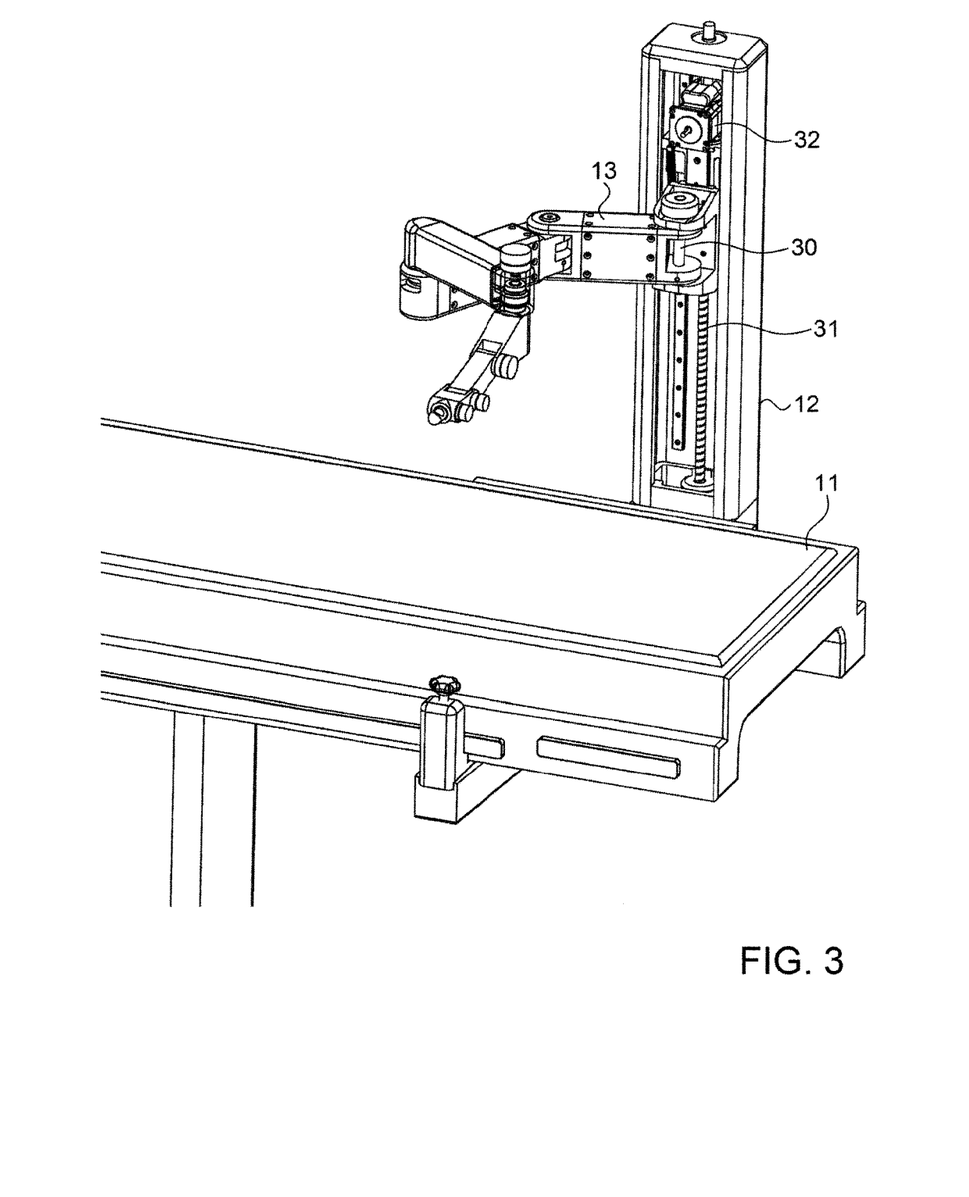
FIG. 3 shows schematically a cutaway view of the bed mounted base of the system of FIG. 1, showing the internal electromechanical components used for controlling motion of the mechanical mounting member.

Reference is now made to FIG. 3, which shows a cutaway view of the bed mounted base 12, to show one possible implementation of the internal electromechanical components used for controlling motion of the mechanical mounting member 13. In this implementation, the mechanical mounting member has a vertical pivot 30 such that it can rotate in the horizontal plane parallel to the bed 11. The vertical motion is provided by a lead screw 31, whose rotation is generated by a servo motor 32, which receives its input commands from the system controller 21, shown in FIG. 2.

Figure 4:
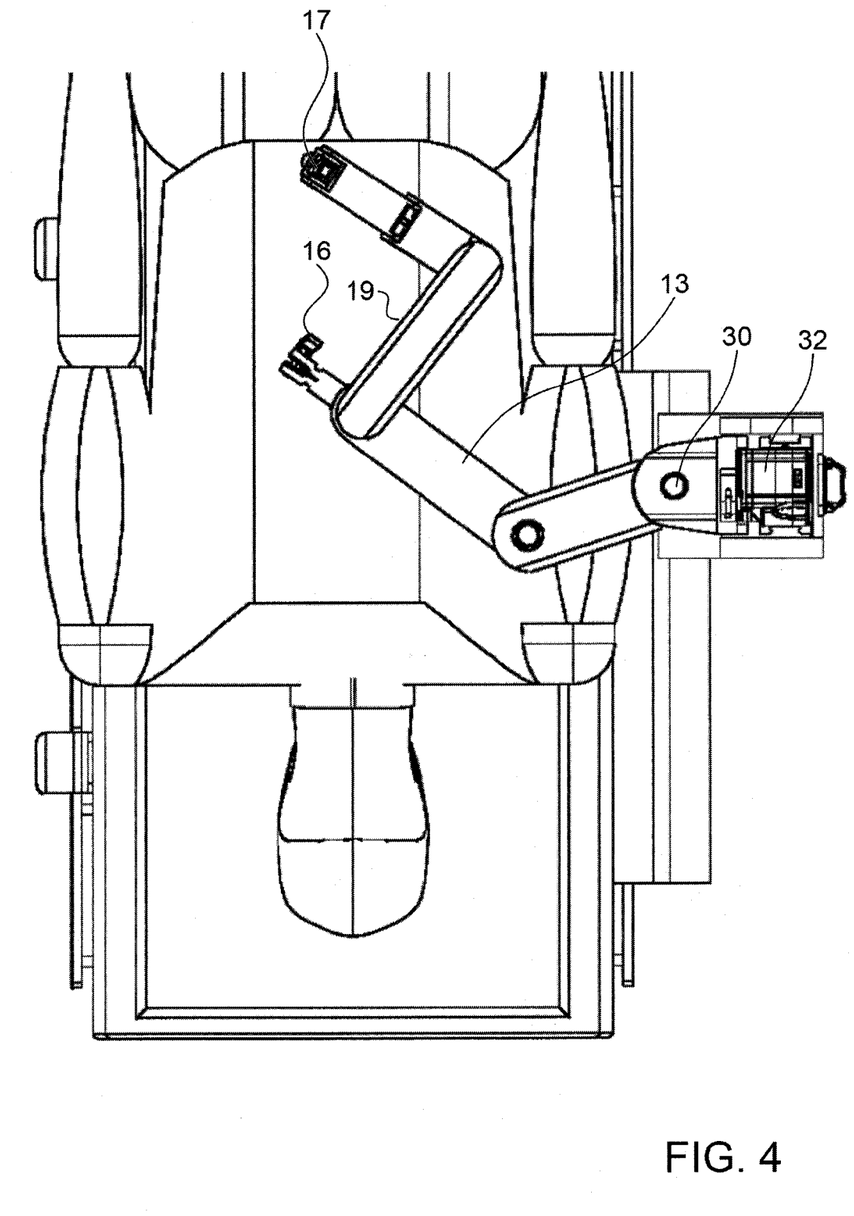
FIG. 4 shows schematically a top view of the system shown in FIG. 3, positioned above a patient lying on the operating table.

Reference is now made to FIG. 4, which shows a top view of the system shown in FIG. 3, positioned above the patient 10 lying on the bed 11. This view shows a K-wire 16 attaching the mechanical mounting member 13 to a bone in the spine of the patient such that the mechanical mounting member moves up and down with the breathing of the patient. In this implementation, the mechanical mounting member 13 is shown attached to a number of articulated robotic arms 19. The robotic actuator 17 is positioned over the lower spine of the patient for performing the desired operation.

In the implementations shown hereinabove, the servo motor is shown controlling vertical translational motion of the mechanical mounting member relative to the bed support base. A motor can also alternatively be used to control the orientation angle of the pivot joint 14 shown in FIG. 1. In that implementation rise and fall of the patient's spine causes the mechanical mounting member to pivot around the joint 14, and when excessive force is detected on the K-wire, the motor controlling the angle of swivel comes into operation in order to reduce the force on the K-wire.

Since the surgeon can work on the vertebrae at angles other than the directly vertical orientation, in such cases there are lateral forces applied to the tool guide, which too could degrade the integrity of the mechanical connection between the bone and the mechanical mounting member. Therefore it is important to be able to measure and counteract such lateral forces also, and this can be done by incorporation of additional sensors which can be installed on the connection between the K wire and the mechanical mounting member, or on the tool guide itself. In such a situation the additional servo control motors should be installed within the bed mounted base, in order to protect against excessive forces also in the lateral directions. In order to provide full protection against any force applied by the surgeon on the patient's bone, all 6 degrees of freedom should be sensed and corrected, using six sensors on the K wire for instance, and the corresponding number of servo motors in the bed mounted base. Each of these servomotors then operates on a joint orientation corresponding to the orientation of the force measured on the patient.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A system for performing an orthopedic operation on a subject, said system comprising:
    a mechanical mounting member adapted to support a surgical tool guide for use in operating on the subject;
    a support member rigidly positioned relative to a bed on which the subject is lying, said mechanical mounting member being attached to said support member by a moveable element having a controlled motion drive;
    a bone attachment element attaching said mechanical mounting member to a bone of the subject in a region where said orthopedic operation is to be performed, such that said mechanical mounting member and its supported tool guide can move with motion of said bone of said subject;
    a force sensor associated with said bone attachment element, said force sensor adapted to output a force signal in accordance with a first force exerted on said bone attachment element; and
    control circuitry receiving said force signal and adapted, when said force exceeds a predetermined threshold level, to output a drive signal to said controlled motion device such that a reactive second force is applied to said mechanical mounting member to counteract said first force exerted on said bone attachment element.

2. A system according to claim 1, wherein said moveable element comprises a linear motion slide, such that said mechanical mounting element can move translationally relative to said support member.

3. A system according to claim 1, wherein said moveable element comprises an angular pivot joint, such that said mechanical mounting element can pivot relative to said support member.

4. A system according to claim 1, wherein said tool guide is mounted directly on said mechanical mounting member.

5. A system according to claim 1, wherein said tool guide is mounted on a robot attached to said mechanical mounting member.

6. A system according to claim 5, wherein said robot comprises a serial arrangement of controlled articulated arms attached to said mechanical mounting member.

7. A system according to claim 1, wherein said movable element is adapted to enable said tool guide to rise and fall together with vertical motion of said bone of the subject when said controlled motion drive is not actuated.

8. A system according to claim 1, wherein said bone attachment element is a K-wire.

9. A system according to claim 1, wherein said controlled motion drive is set in a free-running condition when said first force exerted on said bone attachment element is less than said predetermined threshold level, such that said mechanical mounting member can move freely with motion of said bone.

10. A system according to claim 1 wherein said first force exerted on said bone attachment element results from force applied by a surgical tool in said tool guide.

11. A method of performing orthopedic surgery on a subject, comprising:
    supporting a surgical tool guide by a mechanical mounting member, for use in performing said surgery;
    attaching an end of said mechanical mounting member remote from said tool guide, to a support member rigidly positioned relative to a bed on which the subject is lying, by means of a moveable element having a controlled motion drive;
    attaching a bone attachment element between said mechanical mounting member and a bone of the subject a where said orthopedic surgery is to be performed, such that mechanical mounting member and said tool guide can move together with movement of said bone of the subject;
    measuring a first force present in said bone attachment element; and
    if said first force exceeds a predetermined threshold level, actuating said controlled motion drive such that a reactive second force is applied to said mechanical mounting member to counteract said first force exerted on said bone attachment element.

12. A method according to claim 11, wherein said moveable element comprises a linear motion slide, such that said mechanical mounting element can move translationally relative to said support member.

13. A method according to claim 11, wherein said moveable element comprises an angular pivot joint, such that said mechanical mounting element can pivot relative to said support member.

14. A method according to claim 11, wherein said tool guide is mounted directly on said mechanical mounting member.

15. A method according to claim 11, wherein said tool guide is mounted on a robot attached to said mechanical mounting member.

16. A method according to claim 15, wherein said robot comprises a serial arrangement of controlled articulated arms attached to said mechanical mounting member.

17. A method according to any of claims 11 to 16, wherein said movable element enables said tool guide to rise and fall together with vertical motion of said bone of the subject when said controlled motion drive is not actuated.

18. A method according to claim 11, wherein said bone attachment element is a K-wire.

19. A method according to claim 11, wherein said controlled motion drive is set in a free-running condition when said first force exerted on said bone attachment element less than said predetermined threshold level, such that said mechanical mounting member can move freely with motion of said bone.

20. A method according to claim 11 wherein said first force exerted on said bone attachment element results from force applied by a surgical tool in said tool guide.

* * * * *